US00PP14719P2

(12) United States Plant Patent
Akiyama et al.

(10) Patent No.: US PP14,719 P2
(45) Date of Patent: Apr. 20, 2004

(54) CALIBRACHOA PLANT NAMED 'ILLUMINATION LIGHT PINK'

(50) Latin Name: *Calibrachoa sp.*
Varietal Denomination: Illumination Light Pink

(75) Inventors: Yasuo Akiyama, Kazo (JP); Ayumi Yoma, Kaminokawa-machi (JP); Daigaku Takeshita, Utsunomiya (JP); Saori Watanabe, Ujiie-machi (JP)

(73) Assignees: Tokita Seed Company, Ltd., Saitama-Ken (JP); Kirin Brewery Co., Ltd., Chuo-ku (JP)

( * ) Notice: Subject to any disclaimer, the term of this patent is extended or adjusted under 35 U.S.C. 154(b) by 0 days.

(21) Appl. No.: 10/437,943

(22) Filed: May 13, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Calibrachoa plant named 'Illumination Light Pink', characterized by its cascading and prostrate plant habit; freely branching growth habit; freely flowering habit; light purple-colored flowers with pale yellow-colored throat with a dark violet-color band at the top of the throat; and good weather tolerance.

1 Drawing Sheet

Botanical classification/cultivar designation: *Calibrachoa sp.* cultivar Illumination Light Pink.

BACKGROUND OF THE INVENTION

The present Invention relates to a new and distinct cultivar of Calibrachoa plant, botanically known as *Calibrachoa sp.*, and hereinafter referred to by the name 'Illumination Light Pink'.

The new Calibrachoa is a product of a planned breeding program conducted by the Inventors in Saitama-ken, Japan. The objective of the breeding program is to create new Calibrachoa cultivars that have stronger growth habit and attractive flower coloration.

The new Calibrachoa originated from a cross-pollination made by the Inventors in August, 1998, in Saitama-ken, Japan, of two unnamed proprietary Calibrachoa seedling selections, not patented. The new Calibrachoa was discovered and selected by the Inventors as a single flowering plant within the progeny of the stated cross-pollination grown in a controlled environment in Saitama-ken, Japan, in May, 2000. The selection of this plant was based on its strong plant growth habit and attractive flower coloration.

Asexual reproduction of the new cultivar by terminal cuttings taken in a controlled environment in Saitama-ken, Japan, since May, 2000, has shown that the unique features of this new Calibrachoa are stable and reproduced true to type in successive generations.

SUMMARY OF THE INVENTION

Plants of the cultivar Illumination Light Pink have not been observed under all possible environmental conditions. The phenotype may vary somewhat with variations in environment such as temperature and light intensity without, however, any variance in genotype.

The following traits have been repeatedly observed and are determined to be the unique characteristics of 'Illumination Light Pink'. These characteristics in combination distinguish 'Illumination Light Pink' as a new and distinct cultivar of Calibrachoa:

1. Cascading and prostrate plant habit.
2. Freely branching growth habit.
3. Freely flowering habit.
4. Light purple-colored flowers with pale yellow-colored throat with a dark violet-colored band at the top of the throat.
5. Good weather tolerance; tolerant to wind, rain, and low and high temperatures.

Plants of the new Calibrachoa can be compared to plants of the female parent, an unnamed proprietary Calibrachoa selection. In side-by-side comparisons conducted by the Inventors in Saitama-ken, Japan, plants of the new Calibrachoa differed from plants of the female parent selection in the flowering characteristics:

1. Plants of the new Calibrachoa were more prostrate in plant habit than plants of the female parent selection.
2. Plants of the new Calibrachoa had larger flowers than plants of the female parent selection.
3. Plants of the new Calibrachoa and the female parent selection differed in flower coloration as plants of the female parent selection had white-colored flowers.

Plants of the new Calibrachoa can also be compared to plants of the male parent, an unnamed proprietary Calibrachoa selection. In side-by-side comparisons conducted by the Inventors in Saitama-ken, Japan, plants of the new Calibrachoa differed from plants of the male parent selection in the flowering characteristics:

1. Plants of the new Calibrachoa had larger flowers than plants of the male parent selection.
2. Plants of the new Calibrachoa and the male parent selection differed in flower coloration as plants of the male parent selection had rose pink-colored flowers.

Plants of the new cultivar can also be compared to plants of the cultivar Illumination Rose 2, disclosed in U.S. Plant patent application Ser. No. 10/094,319. In side-by-side comparisons conducted in Saitama-ken, Japan, plants of the new Calibrachoa differed from plants of the cultivar Illumination Rose 2 in the following characteristics:

1. Plants of the new Calibrachoa were not as prostrate in plant habit as plants of the cultivar Illumination Rose 2.
2. Plants of the new Calibrachoa flowered later than plants of the cultivar Illumination Rose 2.
3. Plants of the new Calibrachoa had slightly larger flowers than plants of the cultivar Illumination Rose 2.
4. Plants of the new Calibrachoa and the cultivar Illumination Rose 2 differed in corolla coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new Calibrachoa.

The photograph at the top of the first sheet comprises a side perspective view of a typical flowering plant of 'Illumination Light Pink'.

The photograph at the bottom of the comprises a close-up view of typical flowers of 'Illumination Light Pink'.

DETAILED BOTANICAL DESCRIPTION

In the following description, color references are made to The Royal Horticultural Society Colour Chart, 1995 Edition, except where general terms of ordinary dictionary significance are used. Plants grown in one-gallon containers were used for the aforementioned photographs and the following description. Plants were grown under conditions which closely approximate commercial production conditions during the winter and early spring in Santa Paula, Calif. in a polyethylene-covered greenhouse. Plants were about four months old when the photographs and description were taken. During the production period, day temperatures ranged from 21 to 29° C., night temperatures ranged from 16 to 20° C., and maximum light levels were about 6,500 footcandles.

Botanical classification: *Calibrachoa sp.* cultivar Illumination Light Pink.

Parentage: Cross-pollination of two unnamed proprietary selections of *Calibrachoa sp.*, not patented.

Propagation:

*Type cutting.*—Terminal vegetative cuttings.

*Time to initiate roots.*—Summer: About 3 days at 25° C. Winter: About 7 days at 20° C.

*Time to produce a rooted young plant.*—Summer: About 21 days at 25° C. Winter: About 28 days at 22° C.

*Root description.*—Fine, fibrous, and white in color.

*Rooting habit.*—Freely branching; dense.

Plant description:

*Form.*—Annual flowering plant; cascading and prostrate plant habit; low mounded; dense and bushy appearance.

*Plant height (from soil level to top of plant plane).*—About 16 cm.

*Plant diameter (area of spread).*—About 68 cm.

*Growth rate.*—Moderate to rapid.

*Branching habit.*—Freely basal branching, about ten basal branches per plant; lateral branches develop at potentially every node; pinching is typically not required.

*Lateral branch description.*—Length: About 58 cm. Diameter: About 4 mm. Internode length: About 1.3 to 3.7 cm. Orientation: Initially upright, then nearly horizontal. Texture: Pubescent; short, fine hairs. Strength: Strong, but flexible. Color: 145B.

*Foliage description.*—Arrangement: Alternate before flowering; when flowering, opposite; simple. Length: About 3 cm. Width: About 1.5 cm. Shape: Elliptic. Apex: Broadly acute. Base: Attenuate. Margin: Entire. Texture, upper and lower surfaces: Slightly glandular and slightly pubescent. Venation pattern: Pinnate; arcuate. Color: Developing, upper and lower surfaces: 147B. Fully expanded foliage, upper surface: 147A. Fully expanded foliage, lower surface: 147B. Venation, upper surface: 147B. Venation, lower surface: 147C. Petiole length: About 3 mm. Petiole diameter: About 2 mm. Petiole color: 145B.

Flower description:

*Flower type and habit.*—Flowers face upright or outwardly; flowers solitary and axillary; salverform. Freely flowering habit, about 20 to 25 flowers and flower buds per lateral stem. Flowers persistent.

*Fragrance.*—None detected.

*Natural flowering season.*—Spring until frost in the autumn; flowering continuous during this period.

*Time to flower.*—Plants begin flowering about ten weeks after planting.

*Flower longevity on the plant.*—About one week.

*Flower size.*—Diameter: About 3.7 cm. Tube length: About 3 cm.

*Flower buds (at stage of showing color).*—Length: About 2.2 cm. Diameter: About 6 mm. Shape: Oblong. Color: 79C.

*Corolla.*—Arrangement/appearance: Single whorl of five petals, fused into flared trumpet. Petal length from throat: About 1.5 cm. Petal width: About 1.7 cm. Petal shape: Fan-shaped to obovate. Petal apex: Rounded to obtuse. Petal margin: Entire. Petal texture: Smooth, glabrous; velvety. Color: Petal, when opening, upper surface: 78A. Petal, when opening, lower surface: 77B to 77C. Petal, fully opened flower, upper surface: 78B; towards throat, 78A; irregular band of 86B at top of throat; venation, 80B. Main color becoming closer to 80C to 80D with development. Petal, fully opened flower, lower surface: 77C to 77D. Flower throat (inside): 11B to 11C. Flower tube (outside): 77C to 77D.

*Sepals.*—Arrangement/appearance: Single whorl of five sepals fused at base; star-shaped. Length: About 7 mm. Width: About 3 mm. Shape: Narrowly elliptic to lanceolate. Apex: Acute. Margin: Entire. Texture, upper and lower surfaces: Smooth, glabrous. Color: Developing and fully expanded, upper surface: 146A. Developing and fully expanded, lower surface: 146A.

*Peduncles.*—Length: About 3 cm. Width: About 1 mm. Strength: Moderately strong. Angle: About 45 to 60° from stem. Texture: Pubescent. Color: 144B.

*Reproductive organs.*—Stamens: Quantity per flower: Typically five. Anther shape: Oval. Anther length: Less than 1 mm. Anther color: 10A. Pollen amount: Scarce. Pollen color: 10A. Pistils: Quantity per flower: One. Pistil length: About 9 mm. Stigma shape: Anvil-shaped; curved. Stigma color: 144B.

Style length: About 5 mm. Style color: 144C. Ovary color: 145A.

*Seed/fruit.*—Seed and fruit production has not been observed.

Disease/pest resistance: Plants of the new Calibrachoa have not been noted to be resistant to pathogens and pests common to Calibrachoa.

Weather/temperature tolerance: Plants of the new Calibrachoa are tolerant to rain and wind and have been observed to tolerate temperatures from 3 to 35° C.

It is claimed:

1. A new and distinct cultivar of Calibrachoa plant named 'Illumination Light Pink', as illustrated and described.

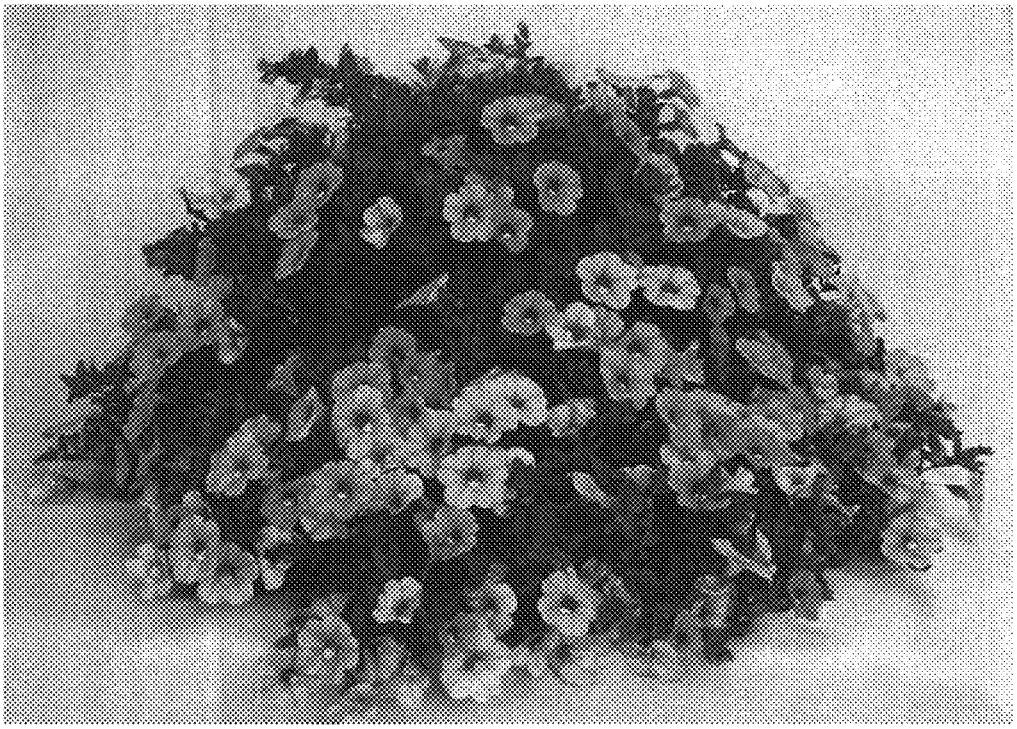
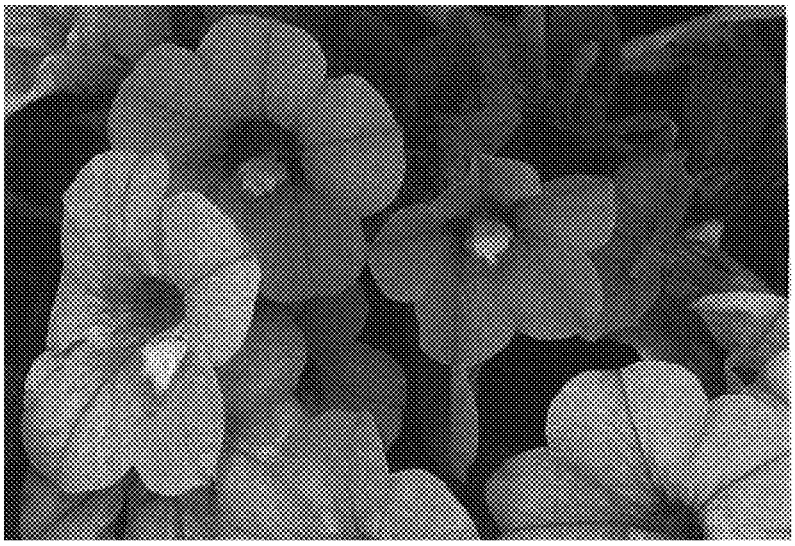

* * * * *